(12) United States Patent
Ueda et al.

(10) Patent No.: US 7,262,330 B2
(45) Date of Patent: Aug. 28, 2007

(54) PROCESS OF PRODUCING ALDEHYDES

(75) Inventors: Akio Ueda, Okayama (JP); Yuuichi Fujita, Okayama (JP); Hirotaka Kawasaki, Okayama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 939 days.

(21) Appl. No.: 10/656,181

(22) Filed: Sep. 8, 2003

(65) Prior Publication Data
US 2004/0054236 A1 Mar. 18, 2004

Related U.S. Application Data

(63) Continuation of application No. PCT/JP01/08573, filed on Sep. 28, 2001.

(30) Foreign Application Priority Data
Mar. 8, 2001 (JP) ............................ 2001-064880

(51) Int. Cl.
C07C 45/50 (2006.01)
(52) U.S. Cl. .................................... 568/454
(58) Field of Classification Search ................ 568/454
See application file for complete search history.

(56) References Cited

U.S. PATENT DOCUMENTS

| | | | | |
|---|---|---|---|---|
| 3,839,378 | A | 10/1974 | Yamaguchi et al. | 260/413 |
| 4,041,082 | A | 8/1977 | Onoda et al. | 260/604 |
| 4,244,882 | A | 1/1981 | Isa et al. | 260/410.6 |
| 4,322,314 | A | 3/1982 | Onoda et al. | 252/412 |
| 4,528,403 | A | 7/1985 | Tano et al. | 568/454 |
| 4,822,917 | A | 4/1989 | Miyazawa et al. | 568/454 |
| 5,099,047 | A | 3/1992 | Sato et al. | 556/136 |
| 5,105,018 | A | 4/1992 | Miyazawa et al. | 568/453 |
| 5,189,105 | A | 2/1993 | Miyazawa et al. | 252/182.12 |
| 5,227,532 | A | 7/1993 | Sato et al. | 568/454 |
| 5,235,113 | A | 8/1993 | Sato et al. | 568/454 |
| 5,306,839 | A | 4/1994 | Sato et al. | 550/70 |
| 5,362,917 | A | 11/1994 | Ogawa et al. | 568/454 |
| 5,364,445 | A | 11/1994 | Sakamoto et al. | 75/426 |
| 5,391,801 | A | 2/1995 | Sato et al. | 558/156 |
| 5,414,160 | A | 5/1995 | Sato et al. | 568/883 |
| 5,426,238 | A | 6/1995 | Mori et al. | 568/454 |
| 5,468,419 | A | 11/1995 | Miyazawa et al. | 252/182.12 |
| 5,550,302 | A | 8/1996 | Mori et al. | 568/881 |
| 5,633,418 | A | 5/1997 | Sato et al. | 585/513 |
| 5,648,553 | A | 7/1997 | Ueda et al. | 568/454 |
| 5,648,554 | A | 7/1997 | Mori et al. | 568/454 |
| 5,663,403 | A | 9/1997 | Sato et al. | 558/156 |
| 5,667,644 | A | 9/1997 | Mori et al. | 203/17 |
| 5,672,766 | A | 9/1997 | Mori et al. | 568/454 |
| 5,728,861 | A | 3/1998 | Sato et al. | 568/454 |
| 5,865,957 | A | 2/1999 | Ueda et al. | 203/25 |
| 5,910,600 | A | 6/1999 | Urata et al. | 558/162 |
| 5,936,130 | A | 8/1999 | Mori et al. | 568/454 |
| 6,172,267 | B1 | 1/2001 | Urata et al. | 568/454 |
| 6,265,620 | B1 | 7/2001 | Urata et al. | 568/454 |
| 6,291,717 | B1 | 9/2001 | Takai et al. | 568/454 |
| 6,444,863 | B2 | 9/2002 | Ueda et al. | 568/882 |
| 6,455,743 | B1 | 9/2002 | Ueda et al. | 568/881 |
| 6,583,324 | B2 | 6/2003 | Takai et al. | 568/451 |
| 6,610,891 | B1 | 8/2003 | O'Young et al. | 568/451 |

FOREIGN PATENT DOCUMENTS

| | | |
|---|---|---|
| GB | 1 440 413 | 6/1976 |
| JP | 8-10624 | 1/1996 |
| JP | 2001-316320 | 11/2001 |
| JP | 2001-342164 | 12/2001 |

*Primary Examiner*—Sikarl A. Witherspoon
(74) *Attorney, Agent, or Firm*—Oblon, Spivak, McClelland, Maier & Neustadt, P.C.

(57) ABSTRACT

A process of producing aldehydes in a continuous hydroformylation process of continuously reacting an olefinic unsaturated compound with carbon monoxide and hydrogen in the presence of a rhodium-phosphite based complex catalyst and continuously separating at least one component from a reaction product, the process being characterized in that at least a part of an aldehyde product and water are taken out as a mixed vapor flow from a catalyst-existent region in the process, and at least a part thereof is fed outside the catalyst-existent region as it stands as the vapor or as a condensate after cooling, to reduce the water concentration within the catalyst-existent region, whereby decomposition of phosphite ligands in the hydroformylation process of olefins is suppressed.

14 Claims, 3 Drawing Sheets

PROCESS OF PRODUCING ALDEHYDES

TECHNICAL FIELD

The present invention relates to a process of producing aldehydes by a hydroformylation reaction of an olefinic unsaturated compound in the presence of a rhodium-phosphite based complex catalyst.

BACKGROUND ART

Processes of producing aldehydes by hydroformylation of an olefinic unsaturated compound with carbon monoxide and hydrogen in the presence of a Group VIII metal complex catalyst are widely industrialized. As the catalyst in this hydroformylation reaction, complex catalysts comprising a Group VIII metal such as rhodium, modified with a ligand such as compounds of trivalent phosphorus are used, and for enhancing activity and selectivity of the hydroformylation reaction, various ligands are studied. For example, JP-B-45-10730 discloses that rhodium complex catalysts modified with a trivalent phosphorus ligand such as triarylphosphines and triaryl phosphites are effective. Above all, it is known that catalysts modified with a phosphite ligand exhibit high activity and sensitivity in the hydroformylation reaction.

However, as disclosed in JP-A-59-51229, it is known that in phosphite ligands such as triphenyl phosphite, the ligand relatively rapidly decomposes in the hydroformylation reaction system, resulting in a reduction of catalytic activity, and it is necessary to continuously supplement the phosphite ligands. Accordingly, not only for improving the activity and selectivity of the catalyst but also for minimizing the reduction of catalytic activity due to a loss of the phosphite ligands, there are proposed various kinds of phosphite ligands.

For example, cyclic phosphite ligands containing a phosphorus atom in the bridge head portion thereof (JP-A-59-51228 and JP-A-59-51230), triaryl phosphite ligands having a substituent in a specific site of the benzene ring (JP-A-57-123134), triaryl phosphite ligands having a substituent in a specific site of the naphthyl ring (JP-A-4-288033), and diorganophosphite ligands having a cyclic structure containing a phosphorus atom within a molecule thereof (JP-T-61-501268) are proposed. In addition, there are known methods of using, as examples of bisphosphite ligands and polyphosphite ligands, diorganophosphite ligands (JP-A-62-116535 and JP-A-62-116587) and bisphosphite ligands having a cyclic structure (JP-A-4-290551) and a method of using cyclic structure-free bisphosphite ligands and polyphosphite ligands by the present applicant (JP-A-5-178779).

However, as described previously, nevertheless the phosphite ligands exhibit high activity and excellent selectivity in the hydroformylation reaction, for industrially advantageously producing aldehydes, stability of the phosphite ligands themselves was problematic. That is, rapid decomposition of the phosphite ligands involved problems such that not only it adversely affects the activity and stability of catalyst, but also new phosphite ligands must be continuously supplemented.

In addition to the foregoing JP-A-59-51229, for example, JP-T-61-501268 describes that triphenyl phosphite rapidly reacts with an aldehyde at room temperature even in the absence of rhodium. It is thought that a defect of triorganophosphites such as triphenyl phosphite is caused by the matter that the triorganophosphites have a very high affinity to react with aldehydes. Further, it is described that products obtained by reaction of triorganophosphites with aldehydes are readily hydrolyzed to form corresponding hydroxyalkylphosphonic acids. In diorganophosphites, it is described that though the formation speed of products obtained by reaction of diorganophosphites with aldehydes is slow, acid by-products are formed like the foregoing case.

Such hydroxyalkylphosphonic acids are formed by an autocatalytic process, and especially, are liable to be formed in a continuous catalytic recirculation process wherein contact of phosphite ligands with aldehyde products extends over a long period of time. Since such hydroxyalkylphosphonic acids are in general insoluble in liquid hydroformylation reaction media, they are rapidly accumulated in the process to precipitate gelatin-like by-products, so that they may possibly clog or stain circulation conduits of the continuous hydroformylation reaction.

For removing such precipitates by an arbitrary proper method such as a method of acid extraction with weak bases such as sodium bicarbonate, it is necessary to periodically stop or pause the operation of the process. It may be said that such a phenomenon is a characteristic feature inherent to phosphite based ligands, which is not seen in conventionally industrially employed phosphine based ligands such as triphenylphosphine.

As methods of solving the problem of stability of these phosphite ligands, for example, JP-A-60-156636 discloses a method of adding tertiary amines for neutralizing acidic substances formed by decomposition of phosphite ligands. Further, JP-T-61-501268 discloses a method of minimizing decomposition of phosphite ligands by removing acidic substances with weakly basic anion exchange resins. In addition, JP-B-5-48215 discloses that metallization of rhodium is depressed by distillation in the presence of a specific polar functional group-containing organic polymer and discloses that in distillation and separation of aldehyde products from reaction products containing a rhodium-phosphite based complex catalyst, it is desired that the distillation and separation are carried out at a temperature of lower than 150° C., and preferably lower than 140° C. JP-A-6-199729 discloses a method of stabilizing phosphite ligands against decomposition by adding epoxides. JP-A-6-199728 discloses a method of using added water and/or weakly acidic additives as additives for enhancing catalytic activity of a specific rhodium-bisphosphite complex catalyst. Moreover, JP-A-8-165266 discloses a method in which in separating at least one component selected from carbon monoxide, hydrogen, an unreacted olefinic unsaturated compound, an aldehyde product, a solvent, a middle boiling point by-product, and a high boiling point by-product from a reaction product containing the aldehyde product by a separation operation, the separation operation is carried out within a certain defined range of a parameter obtained from the temperature and residence time in the separation operation, whereby a loss of phosphite ligands and formation of by-products are effectively suppressed. Also, it is disclosed that in the case where the foregoing separation operation is steam distillation, when the separation operation is carried out within a certain defined range of a parameter obtained from the steam distillation temperature, residence time and steam fraction in the separation operation, decomposition of the phosphite ligands is suppressed.

In the light of the above, in the conventional technologies, some added substances or post-treatment methods were required. Further, though ones in which the operation conditions in the separation step are defined were known, they did not provide a process of substantially suppressing the decomposition of phosphite ligands.

Further, the foregoing JP-A-6-199728 discloses that a part of bisphosphite ligand catalysts is accelerated in catalytic activity by the addition of water. But, in general, it is known that as in triphenyl phosphite described in JP-T-61-501268, decomposition products of phosphite ligands are formed in the presence of water, and further decomposition of the decomposition products proceeds.

However, a little of water is in general present in the hydroformylation reaction system. This is because not only in the hydroformylation reaction system, a condensation dehydration reaction takes place as a side reaction to form water as a by-product, but also water that is entrained with a mixed gas of hydrogen and carbon monoxide (the mixed gas being hereinafter referred to as "oxo gas") as raw materials and incorporated in the hydroformylation reaction system is not negligible. The concentration of water to be entrained in the oxo gas varies depending on the kind and operation conditions of the oxo gas manufacture step. For example, in the case where methane or naphtha is subjected to a steam reforming reaction and a water gas reaction, or a partial oxidation reaction together with carbon dioxide, water vapor, etc. at high temperatures of about 800° C. to obtain a decomposed gas comprising hydrogen, carbon monoxide, carbon dioxide, water vapor, etc., and the decomposed gas is then introduced into an absorption column and subjected to absorption and removal of carbon dioxide by an alkanolamine or a hot potassium carbonate aqueous solution (hereinafter referred to as "decarbonation step") to obtain a purified oxo gas, since the obtained purified oxo gas contains a saturated water vapor under the operation pressure and temperature conditions of the absorption column in the decarbonation step, even when a major part of water is removed by compression and cooling condensation in an after step, from 0.2 to 0.7% by volume of water is generally carried as the water vapor, and therefore, this water is incorporated into the hydroformylation reaction system. Further, in the step of separating and recovering the catalyst, when a catalyst-containing solution (hereinafter referred to as "catalyst liquid") is subjected to contact processing with water such as water washing and then circulated and used again for the hydroformylation reaction, water of about a saturated solubility is at least contained in the catalyst liquid, and therefore, when the catalyst liquid is directly fed into the hydroformylation process, water is carried into the process.

In the light of the above, in the hydroformylation reaction using a rhodium-phosphite based complex catalyst, decomposition of phosphite ligands proceeds by water in the process, causing a reduction of the activity of the catalyst.

In addition, it is known that in the hydroformylation reaction using a phosphite based complex catalyst, the reaction temperature can be made low as compared with the case of using a phosphine based complex catalyst because the phosphite based complex catalyst has an activity higher than the phosphine based complex catalyst. Thus, the temperature in the process becomes low, and the amount of water vapor to be purged outside the process becomes small, and therefore, it is thought that the amount of water in the process is high as compared with the case of using the phosphine based catalyst.

As the hydroformylation process, there are generally known a liquid circulation type hydroformylation process in which an olefinic unsaturated compound is continuously reacted with carbon monoxide and hydrogen in the presence of a catalyst, and a reaction product containing the catalyst and an aldehyde product taken out from a reactor is fed into a catalyst separation step to separate the aldehyde product, followed by again circulation into the reactor; and a fixed catalyst type hydroformylation process in which an olefinic unsaturated compound is continuously reacted with carbon monoxide and hydrogen in the presence of a catalyst, a reaction product containing the aldehyde product, unreacted olefinic unsaturated compound and by-products taken out from a reactor is fed into a separator to separate the aldehyde product, and the residue is recirculated into the reactor.

As a method of reducing the amount of water in the process, there may be considered a method in which after separating the aldehyde product from the reaction product containing the catalyst and aldehyde product taken out from the reactor, a part of water is taken outside the process together with the catalyst contained in the reaction product, thereby reducing the amount of the catalyst liquid to be circulated into the reactor, or a method of newly providing a dehydration device. However, according to these methods, a loss of the catalyst becomes large, or the cost for equipment increases, and therefore, these methods are not economical.

Under these circumstances, the invention has been made, and its object is to provide a process of suppressing decomposition of phosphite ligands within a catalyst-existent region in the continuous hydroformylation process using a general rhodium-phosphite based complex as a catalyst, especially to provide a process of producing aldehydes efficiently and economically by reducing water within a catalyst-existent region that will become a cause of decomposition of phosphite ligands.

The present inventors made extensive and intensive investigations about the foregoing problem. As a result, it has been found that in the continuous hydroformylation process, when at least a part of an aldehyde product and water are taken out as a mixed vapor flow from a catalyst-existent region of the hydroformylation process, and at least a part thereof is fed outside the catalyst-existent region and treated as it stands as the vapor or as a condensate after cooling, it is possible to efficiently and economically reduce the water concentration within the catalyst-existent region in the process without causing an increase of a loss of the catalyst or without a need of newly providing a dehydration device, resulting in attaining the invention.

DISCLOSURE OF THE INVENTION

The gist of the invention resides in a process of producing aldehydes in a continuous hydroformylation process of continuously reacting an olefinic unsaturated compound with carbon monoxide and hydrogen in the presence of a rhodium-phosphite based complex catalyst and continuously separating at least one component from a reaction product, the process being characterized in that at least a part of an aldehyde product and water are taken out as a mixed vapor flow from a catalyst-existent region in the process, and at least a part thereof is fed outside the catalyst-existent region as it stands as the vapor or as a condensate after cooling, to reduce the water concentration within the catalyst-existent region.

In the invention, it is preferred that the continuous hydroformylation process is a liquid circulation type hydroformylation process in which a reaction product containing at least the rhodium-phosphite based complex catalyst and aldehyde product taken out from a reactor is fed into a catalyst separation step to separate the aldehyde product, followed by circulation into the reactor.

Further, in the invention, it is preferred that the continuous hydroformylation process is a fixed catalyst type continuous hydroformylation process in which a reaction product containing the aldehyde product, unreacted olefinic unsaturated compound and by-products taken out from a reactor by gas stripping, etc. is fed into a separation step to separate the aldehyde product.

Another gist of the invention resides in a process of producing aldehydes in a liquid circulation type hydroformylation process of taking out a reaction product containing at least a rhodium-phosphite based complex catalyst and an aldehyde product obtained by continuous hydroformylation reaction of an olefinic unsaturated compound with carbon monoxide and hydrogen in the presence of a rhodium-phosphite based complex catalyst from a reactor and feeding it into a counter-current contact column; subjecting it to counter-current contact with a raw material gas to recover the unreacted olefinic unsaturated compound; and after gas-liquid separation, subjecting a liquid phase to separation and recovery of the aldehyde product in a catalyst separation step and then circulating it as a reaction medium into the reactor, the process being characterized in that at least a part of the aldehyde product and water are taken out as a mixed vapor flow from a catalyst-existent region in the process, and at least a part of the mixed vapor flow is taken out as it stands as the vapor or as a condensate after cooling and then fed into a step outside the catalyst-existent region to reduce the water concentration within the catalyst-existing region.

Still another gist of the invention resides in a process of producing aldehydes in a liquid circulation type hydroformylation process of taking out a reaction product containing at least a rhodium-phosphite based complex catalyst and an aldehyde product obtained by continuous hydroformylation reaction of an olefinic unsaturated compound with carbon monoxide and hydrogen in the presence of a rhodium-phosphite based complex catalyst from a reactor; after gas-liquid separation, subjecting the resulting liquid phase to separation and recovery of the aldehyde product in a catalyst separation step and then circulating it as a reaction medium into the reactor; and bringing the aldehyde product separated in the catalyst separation step into counter-current contact with a raw material gas in a counter-current contact column to recover the unreacted olefinic unsaturated compound, the process being characterized in that at least a part of the aldehyde product and water are taken out as a mixed vapor flow from a catalyst-existent region, and at least a part thereof is fed as it stands as the vapor or as a condensate after cooling into a step outside the catalyst-existent region to reduce the water concentration within the catalyst-existing region.

BRIEF DESCRIPTION OF THE DRAWINGS

In FIGS. 1 to 3, numerals 1, 2, 3, 4, 5 and 6 denote a reactor, a counter-current contact column, a gas-liquid separator, a catalyst separation column, a catalyst recovery step, and a condenser, respectively.

BEST MODE FOR CARRYING OUT THE INVENTION

Figure 1:
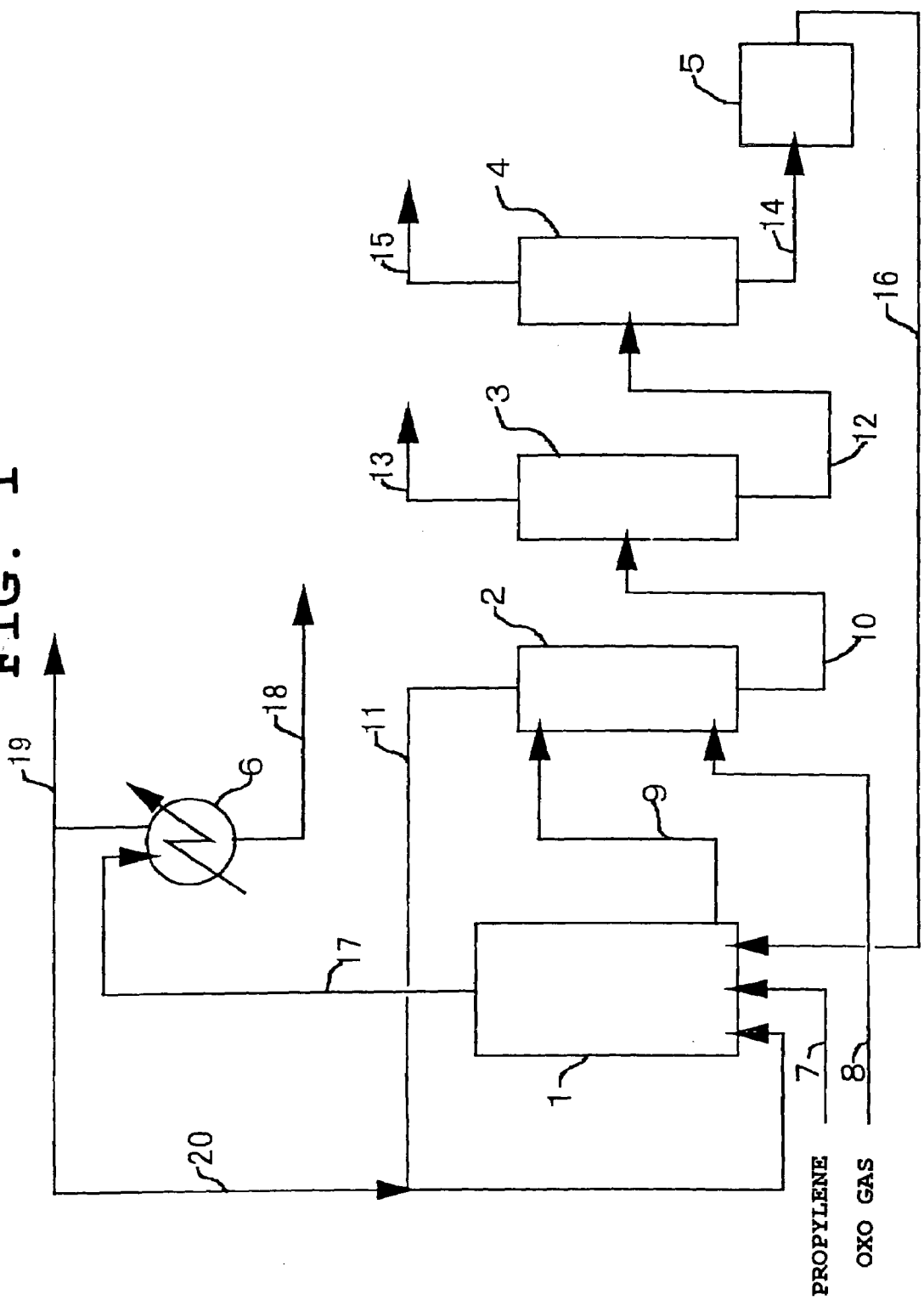
FIG. 1 is a process flow sheet showing one embodiment of a process of the invention.

The invention will be hereunder described in more detail.

In general, the hydroformylation process of the invention is not particularly limited so far as it is a continuous process of continuously reacting an olefinic unsaturated compound with hydrogen and carbon monoxide in the presence of a rhodium-phosphite based complex catalyst using a continuous reactor and continuously separating at least one component from the reaction product. As the kind of reactors, can be used reactors of a stirred vessel type, a bubble column type, a tube type, a gas stripping type, etc.

As the olefinic unsaturated compound to which the hydroformylation reaction of the invention is applied, are preferable usually employed arbitrary α-olefins or internal olefins such as linear olefinic unsaturated compounds and branched chain olefinic unsaturated compounds. Specific examples include α-olefins such as propylene, butene-1, hexene-1, octane-1, dodecene-1, and tetradecene-1, with propylene being particularly preferred.

In the hydroformylation reaction of the invention, a rhodium-phosphite based complex catalyst is used. Concretely, it is preferred to use rhodium complex catalysts containing a trivalent phosphite compound as a ligand. As the trivalent phosphite compound, can be used usually employed arbitrary compounds having an ability as a monodentate ligand or multidentate ligand and capable of being easily decomposed in the presence of water. For example, trivalent phosphite compounds represented by the following formulae (1) to (10) can be used.

(In the formula, $R^1$ to $R^3$ each independently represents an optionally substituted monovalent hydrocarbon group.)

In the formula (1), examples of optionally substituted monovalent hydrocarbon groups include an alkyl group, an aryl group, and a cycloalkyl group.

Specific examples of compounds represented by the formula (1) include trialkyl phosphites such as trimethyl phosphite, triethyl phosphite, n-butyldiethyl phosphite, tri-n-butyl phosphite, tri-n-propyl phosphite, tri-n-octyl phosphite, and tri-n-dodecyl phosphite; triaryl phosphites such as triphenyl phosphite and trinaphthyl phosphite; and alkylaryl phosphites such as dimethylphenyl phosphite, diethylphenyl phosphite, and ethyldiphenyl phosphite. Further, bis(3,6,8-tri-t-butyl-2-naphthyl)phenyl phosphite, bis(3,6,8-tri-t-butyl-2-naphthyl)(4-biphenyl) phosphite, etc. as described in JP-A-6-122642 may be used. Above all, triphenyl phosphite is the most preferable.

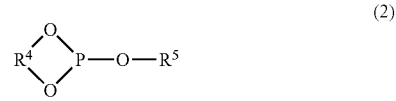

(In the formula, $R^4$ represents an optionally substituted divalent hydrocarbon group; and $R^5$ represents an optionally substituted monovalent hydrocarbon group.)

In the formula (2), examples of optionally substituted divalent hydrocarbon groups represented by $R^4$ include alkylene groups that may contain an oxygen, nitrogen or sulfur atom, etc. in the midway of the carbon chain thereof; cycloalkylene groups that may contain an oxygen, nitrogen or sulfur atom, etc. in the midway of the carbon chain thereof; divalent aromatic groups such as phenylene and naphthylene; divalent aromatic groups in which divalent aromatic rings are connected to each other directly or via an alkylene group or an atom such as oxygen, nitrogen, and sulfur in the midway thereof; and ones in which a divalent aromatic group and an alkylene group are connected to each other directly or via an atom such as oxygen, nitrogen, and sulfur in the midway thereof. Examples of optionally substituted monovalent hydrocarbon groups represented by $R^5$ include alkyl groups, aryl groups, and cycloalkyl groups.

Specific examples of compounds represented by the formula (2) include compounds described in U.S. Pat. No. 3,415,906, such as neopentyl(2,4,6-t-butyl-phenyl) phosphite and ethylene (2,4,6-t-butyl-phenyl) phosphite.

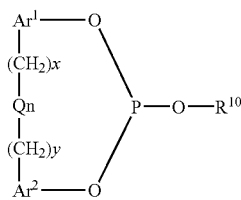

(3)

(In the formula, $R^{10}$ is synonymous with $R^5$ in the formula (2); $Ar^1$ and $Ar^2$ each independently represents an optionally substituted arylene group; x and y each independently represents 0 or 1; Q represents a crosslinking group selected from the group consisting of —$CR^{11}R^{12}$—, —O—, —S—, —$NR^{13}$—, —$SiR^{14}R^{15}$— and —CO—; $R^{11}$ and $R^{12}$ each independently represents a hydrogen atom, an alkyl group having from 1 to 12 carbon atoms, a phenyl group, a tolyl group, or an anisyl group; $R^{13}$, $R^{14}$ and $R^{15}$ each independently represents a hydrogen atom or a methyl group; and n represents 0 or 1.)

Specific examples of compounds represented by the formula (3) include compounds described in U.S. Pat. No. 4,599,206, such as 1,1'-biphenyl-2,2'-diyl-(2,6-di-t-bu-tyl-4-methylphenyl) phosphite; and compounds described in U.S. Pat. No. 4,717,775, such as 3,3'-di-t-butyl-5,5'-dimethoxy-1,1'-biphenyl-2,2'-diyl-(2-t-butyl-4-methoxy-phenyl)phosphite.

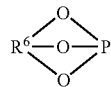

(4)

(In the formula, $R^6$ represents a cyclic or acyclic, optionally substituted trivalent hydrocarbon atoup.)

Specific examples of compounds represented by the formula (4) include compounds described in U.S. Pat. No. 4,567,306, such as 4-ethyl-2,6,7-trioxa-1-phosphabicyclo-[2,2,2]-octane.

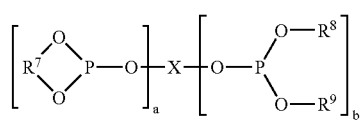

(5)

(In the formula, $R^7$ is synonymous with $R^4$ in the formula (2); $R^8$ and $R^9$ each independently represents an optionally substituted hydrocarbon group; a and b each represents an integer of from 0 to 6; the sum of a and b is from 2 to 6; and X represents a hydrocarbon group having a valence of (a+b).)

Preferred examples of compounds represented by the formula (5) include compounds described in JP-A-2-231497, such as 6,6'-[[3,3',5,5'-tetrakis(1,1'-dimethylethyl)-[1,1'-biphenyl]-2,2'-diyl]bis(oxy)]bis-benzo[d,f][1,3,2]-dioxaphosphebin.

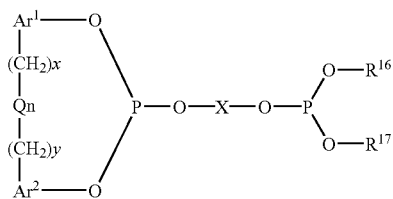

(6)

(In the formula, X represents a divalent group selected from the group consisting of alkylenes, arylenes, and —$Ar^1$—$(CH_2)_x$—$Q_n$—$(CH_2)_y$—$Ar^2$—; and $R^{16}$ and $R^{17}$ each independently represents an optionally substituted hydrocarbon group. $Ar^1$, $Ar^2$, Q, x, y, and n are synonymous with those in the formula (3).)

Specific examples of compounds represented by the formula (6) include compounds described in JP-A-62-116535 and JP-A-62-116587.

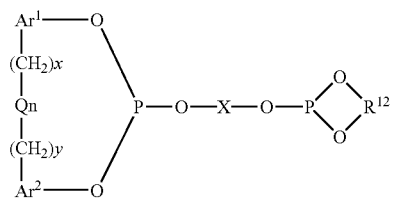

(7)

(In the formula, X, $Ar^1$, $Ar^2$, Q, x, y, and n are synonymous with those in the formula (6); and $R^{18}$ is synonymous with $R^4$ in the formula (2).)

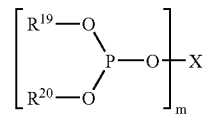

(8)

(In the formula, $R^{19}$ and $R^{20}$ each independently represents an aromatic hydrocarbon group, and at least one aromatic hydrocarbon group of them has a hydrocarbon group in the carbon atom adjacent to the carbon atom to which the oxygen atom is bonded; m represents an integer of from 2 to 4; the respective —O—P($OR^{19}$) ($OR^{20}$) groups may be different from each other; and X represents an optionally substituted hydrocarbon group having a valence of m.)

Of compounds represented by the formula (8), for example, compounds described in JP-A-5-178779 and compounds described in JP-A-10-45776, such as 2,2'-bis(di-1-naphthyl phosphite)-3,3',5,5'-tetra-t-butyl-6,6'-dimethyl-1,1'-biphenyl, are preferable.

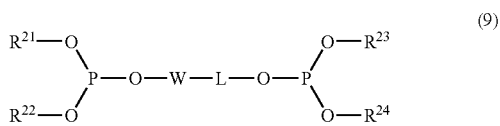

(9)

(In the formula, $R^{21}$ to $R^{24}$ represent an optionally substituted hydrocarbon group, these may be independent upon each other, and $R^{21}$ and $R^{22}$, or $R^{23}$ and $R^{24}$ may be bonded to each other to form a ring; W represents an optionally substituted divalent aromatic hydrocarbon group; and L represents an optionally substituted, saturated or unsaturated divalent aliphatic hydrocarbon group.)

As compounds represented by the formula (9), for example, compounds described in JP-A-8-259578 are used.

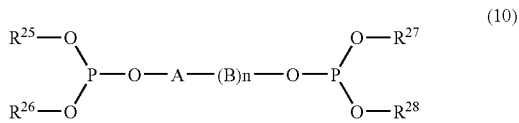

(10)

(In the formula, $R^{25}$ to $R^{28}$ represent an optionally substituted monovalent hydrocarbon group, and $R^{25}$ and $R^{26}$, or $R^{27}$ and $R^{28}$ may be bonded to each other to form a ring; A and B each independently represents an optionally substituted divalent aromatic hydrocarbon group; and n represents an integer of 0 or 1.)

As rhodium sources of the rhodium-phosphite based complex catalyst to be used in combination with such a phosphite compound, are used rhodium complexes such as acetylacetonatorhodium and [Rh(COD) (OAc)]$_2$, organic salts such as rhodium acetate, inorganic salts such as rhodium nitrate, and oxides such rhodium oxide. Here, COD represents cyclooctadiene, and Ac represents an acetyl group.

The rhodium source may be directly fed into the hydroformylation process, but rhodium complex catalysts previously prepared by reacting with carbon monoxide, hydrogen and a phosphite compound in a solvent under high temperature and pressure conditions outside the hydroformylation process may be fed into the hydroformylation process. Usually, the solvent to be used in the preparation of catalysts can be selected from reaction solvents described later but is not always required to be identical with the reaction solvent. The preparation of catalysts is in general carried out under conditions where the pressure is from atmospheric pressure to 100 kg/cm$^2$G, and the temperature is from normal temperature to 150° C.

In the hydroformylation process of the invention, the phosphite compound may be used in an excessive amount and may be present as a free phosphite ligand in the hydroformylation process. For example, the phosphite compound may be used in an amount of one mole or more per mole of rhodium present in the reaction medium, and according to circumstances, the phosphite compound may be used in an amount of up to about 100 moles per mole of rhodium present in the reaction medium or in a larger amount. The reaction medium as referred to herein means a liquid containing the solvent, catalyst, free ligands, olefinic unsaturated compound, aldehyde product, and the like within the reactor.

In general, the sum (amount of the phosphite compound) of the amount of phosphite ligands coordinated (complex formed) with rhodium and the amount of free (non-complex forming) phosphite ligands, the both of which are present in the reaction medium, is usually from about 1 to 500 moles, and preferably from 1 to 100 moles per mole of rhodium. Further, for keeping the amount of the phosphite compound in the reaction medium, phosphite ligands for supplementation may be fed into the reaction medium by an arbitrary method. Moreover, with respect to the phosphite ligands of the rhodium-phosphite based catalyst and the free phosphite ligands, the same kind of ligands is usually used, but as the need arises, individual phosphite ligands may be used, and mixtures of two or more of different phosphite ligands can also be used.

The amount of the rhodium-phosphite based complex catalyst present in the reaction medium of the hydroformylation process of the invention may be an amount in which a sufficient reaction rate is obtained. The rhodium concentration in the reaction medium is usually in the range of from 1 to 1,000 ppm, preferably from 10 to 500 ppm, and more preferably from 25 to 350 ppm in terms of metallic rhodium.

In the hydroformylation reaction of the invention, use of the solvent is not essential, but organic solvents such as toluene or the olefinic unsaturated compound per se as a raw material may be used, and mixtures of two or more thereof can also be used. In general, it is preferred to use the aldehyde product and/or an aldehyde condensation by-product having a high boiling point (hereinafter referred to as "high-boiling product") formed in the hydroformylation reaction process. For example, even in the case where an arbitrary primary solvent is used at the time of initiation of the continuous process, in general, the primary solvent ultimately becomes the aldehyde product and high-boiling product on the nature of the continuous process. If desired, the high-boiling product may be preliminarily formed in the hydroformylation reaction process. The amount of the solvent to be used is not of an important issue in the invention but may be an amount sufficient for keeping a specific rhodium concentration as desired for the prescribed process and making the solvent play a role as the reaction medium. In general, the solvent is used in an amount of from about 5% by weight to about 95% by weight based on the total weight of the reaction medium.

With respect to the hydroformylation reaction conditions of the invention, the hydroformylation process is preferably carried out under a total gas pressure of hydrogen, carbon monoxide and olefinic unsaturated compound of less than 500 kg/cm$^2$G, and more preferably less than 200 kg/cm$^2$G. The minimum total gas pressure is limited by the amount of reaction raw materials necessary for attaining the initial reaction rate. Additionally, in the hydroformylation reaction of the invention, the carbon monoxide partial pressure is preferably from 0.1 to 100 kg/cm$^2$, and more preferably from 1 to 7 kg/cm$^2$; and the hydrogen partial pressure is preferably from 0.1 to 100 kg/cm$^2$, and more preferably from 1 to 8 kg/cm$^2$. In general, a molar ratio of hydrogen to carbon monoxide gas (H$_2$:CO) is from 1:10 to 100:1, and more preferably from 1:10 to 10:1.

Further, the reaction can be usually carried out at a temperature of from 30° C. to 90° C., preferably from 40° C. to 85° C., and more preferably from 50° C. to 80° C. Even when the reaction temperate largely exceeds 90° C., the yield is not so greatly enhanced, and the catalytic activity possibly declines as described in JP-T-61-501268, and therefore, such is in general not preferred.

As the mode of the hydroformylation process of the invention, conventionally known modes can be employed.

For example, there can be employed a liquid circulation type hydroformylation process in which the reaction product containing at least the rhodium-phosphite based complex catalyst and aldehyde product taken out from the reactor is fed into a catalyst separation step to separate the aldehyde product, and the catalyst liquid is then circulated into the reactor.

The liquid circulation type continuous hydroformylation process includes various embodiments and is not particularly limited, but is usually constituted of at least a reaction step and a catalyst separation step. Preferably, it is constituted of at least a reaction step, a catalyst separation step, and a recovery step of unreacted olefin. The catalyst separation step and the recovery step of unreacted olefin may be established in this order or in an opposite order thereto.

The catalyst separation step is a step of separating the aldehyde product from the catalyst liquid. As separation means, arbitrary separation operations and devices such as distillation, evaporation, gas stripping, gas absorption, and extraction can be chosen. Usually, using a distillation column, the aldehyde component is distilled out from the column head, and the catalyst liquid is flown out from the column bottom. Further, with respect to the recovery step of unreacted olefin, arbitrary means and devices can be employed, too, but a counter-current contact column is usually used. A gas-liquid separator and the like are properly provided between the respective devices.

Besides the catalyst separation step and the recovery step of unreacted raw material, a catalyst regeneration step, a purification step such as a rectification column of the aldehyde product, and the like may be included. Further, the reaction product contains the unreacted raw material, solvent, middle-boiling or high-boiling by-products, etc. in addition to the desired aldehyde product. There may be provided a step of separating these compounds by an arbitrary method.

As one example of the specific embodiment of the liquid circulation type hydroformylation process, there may be employed a liquid circulation type hydroformylation process of taking out a reaction product containing at least a rhodium-phosphite based complex catalyst and an aldehyde product obtained by continuous hydroformylation reaction of an olefinic unsaturated compound with carbon monoxide and hydrogen in the presence of a rhodium-phosphite based complex catalyst from a reactor and feeding it into a counter-current contact column; subjecting it to counter-current contact with a raw material gas to recover the unreacted olefinic unsaturated compound; and after gas-liquid separation, subjecting a liquid phase to separation and recovery of the aldehyde product in a catalyst separation step and then circulating it as a reaction medium into the reactor, wherein at least a part of the aldehyde product and water are taken out as a mixed vapor flow from a catalyst-existent region in the process, and at least a part of the mixed vapor flow is taken out as it stands as the vapor or as a condensate after cooling and then fed into a step outside the catalyst-existent region to reduce the water concentration within the catalyst-existing region.

Further, as another example of the specific embodiment of the liquid circulation type hydroformylation process, there may be employed a liquid circulation type hydroformylation process of taking out a reaction product containing at least a rhodium-phosphite based complex catalyst and an aldehyde product obtained by continuous hydroformylation reaction of an olefinic unsaturated compound with carbon monoxide and hydrogen in the presence of a rhodium-phosphite based complex catalyst from a reactor; after gas-liquid separation, subjecting the resulting liquid phase to separation and recovery of the aldehyde product in a catalyst separation step and then circulating it as a reaction medium into the reactor; and bringing the aldehyde product separated in the catalyst separation step into counter-current contact with a raw material gas in a counter-current contact column to recover the unreacted olefinic unsaturated compound, wherein at least a part of the aldehyde product and water are taken out as a mixed vapor flow from a catalyst-existent region, and at least a part thereof is fed as it stands as the vapor or as a condensate after cooling into a step outside the catalyst-existent region to reduce the water concentration within the catalyst-existing region.

In this case, it is possible to feed at least a part of the reaction product containing the unreacted olefinic unsaturated compound, aldehyde product and water taken out from the catalyst-existent region as a mixed vapor flow or condensate into a counter-current contact column outside the catalyst-existing region or the aldehyde separation step, to recover the unreacted olefin and/or aldehyde product. Further, it is possible to take out a part or the whole of the catalyst and solvent as a liquid mixture from the reactor and after distilling off the aldehyde product in the catalyst separation step, circulate the residue as a reaction medium into the reactor. In addition, it is possible to bring the reaction product containing the unreacted olefin, the aldehyde product, etc. into counter-current contact with carbon monoxide and hydrogen to recover the unreacted olefin.

For example, there can be employed a fixed catalyst type continuous hydroformylation process in which the reaction product containing the aldehyde product, unreacted olefinic unsaturated compound and by-products taken out from the reactor by gas stripping, etc. is fed into the separation step to separate the aldehyde product. Further, as the need arises, after separating the aldehyde product from the reaction product, the residue may be recirculated into the reactor.

The fixed catalyst type continuous hydroformylation process includes various embodiments and is not particularly limited, but is usually constituted of at least a reaction step and a separation step of aldehyde product. Further, in the case of the fixed catalyst type continuous hydroformylation process, for reactivating the deactivated catalyst, there may be provided a catalyst reactivation step for taking out a part or the whole of the catalyst from the reaction and reactivating it. Moreover, the reaction product contains the unreacted raw material, solvent, middle-boiling or high-boiling by-products, etc. in addition to the desired aldehyde product. There may be provided a step of separating these components by an arbitrary method. In addition, there may be provided a purification step such as a rectification column of the aldehyde product, and the like.

In the case of the fixed catalyst type continuous hydroformylation process, the amount of the aldehyde contained in the reaction medium and the high-boiling product formed in the reaction process is usually 0.6 or more, and preferably 1 or more in terms of a weight ratio of aldehyde/high-boiling product. When the proportion of the aldehyde is high, the amount of the gas to be used in the stripping may be made low. Therefore, such can make the equipment small-sized and economical.

According to the conventional hydroformylation process, at least a part of the reaction product containing the unreacted olefinic unsaturated compound, aldehyde product and water is taken out as a mixed vapor flow with the unreacted olefinic unsaturated compound gas, etc. from the reaction step and then cooled by a condenser, etc., to form a condensate from a part of water together with the unreacted olefin and aldehyde product, and a part of the condensate is again returned into the reaction step, thereby striving to enhance a conversion of the olefin.

However, in the process of the invention, by taking out at least a part of the aldehyde product and water as a mixed vapor flow from the catalyst-existent region in the process and feeding at least a part of the mixed vapor flow as it stands as the vapor or as a condensate after cooling the vapor outside the catalyst-existing region, it is possible to reduce the water concentration within the catalyst-existent region and to suppress decomposition of the phosphite ligands within the catalyst-existing region. The catalyst-existent region as referred to herein means the range where the catalyst liquid containing the rhodium-phosphite complex catalyst is present and means steps containing the rhodium-phosphite complex catalyst, including the reactor, gas-liquid separator, and catalyst separation step. Accordingly, in the invention, the aldehyde product and water are fed as they stand as the vapor or as a condensate after cooling the vapor are fed outside the catalyst-existent region from a reactor vent gas, a vapor phase of a gas-liquid separator, etc. The feeding outside the catalyst-existent region as referred to herein means a step of feeding into a catalyst-free step or of discharge outside the hydroformylation process.

Specific examples include a method in which the mixed vapor flow containing at least a part of the aldehyde product and water is taken out from the reactor and discharged outside the hydroformylation process; and a method in which the mixed vapor flow containing at least a part of the aldehyde product and water is taken out from the reactor, and at least a part of the mixed vapor flow is discharged as it stands as the vapor or as a condensate after cooling outside the hydroformylation process.

In the invention, the amount of water contained in the mixed vapor flow to be taken out from the catalyst-existent region is 30% or more, and preferably 40% or more of the total amount of water to be fed into the reactor and water to be formed within the reactor. Further, it is desired to feed water contained in the mixed vapor flow to be taken out from the catalyst-existent region in an amount of 30% or more, and preferably 40% or more outside the catalyst-existent region. In addition, the amount of water to be fed outside the catalyst-existent region is 30% or more, and preferably 34% or more of the total amount of water to be fed into the reactor and water to be formed within the reactor.

Figure 2:
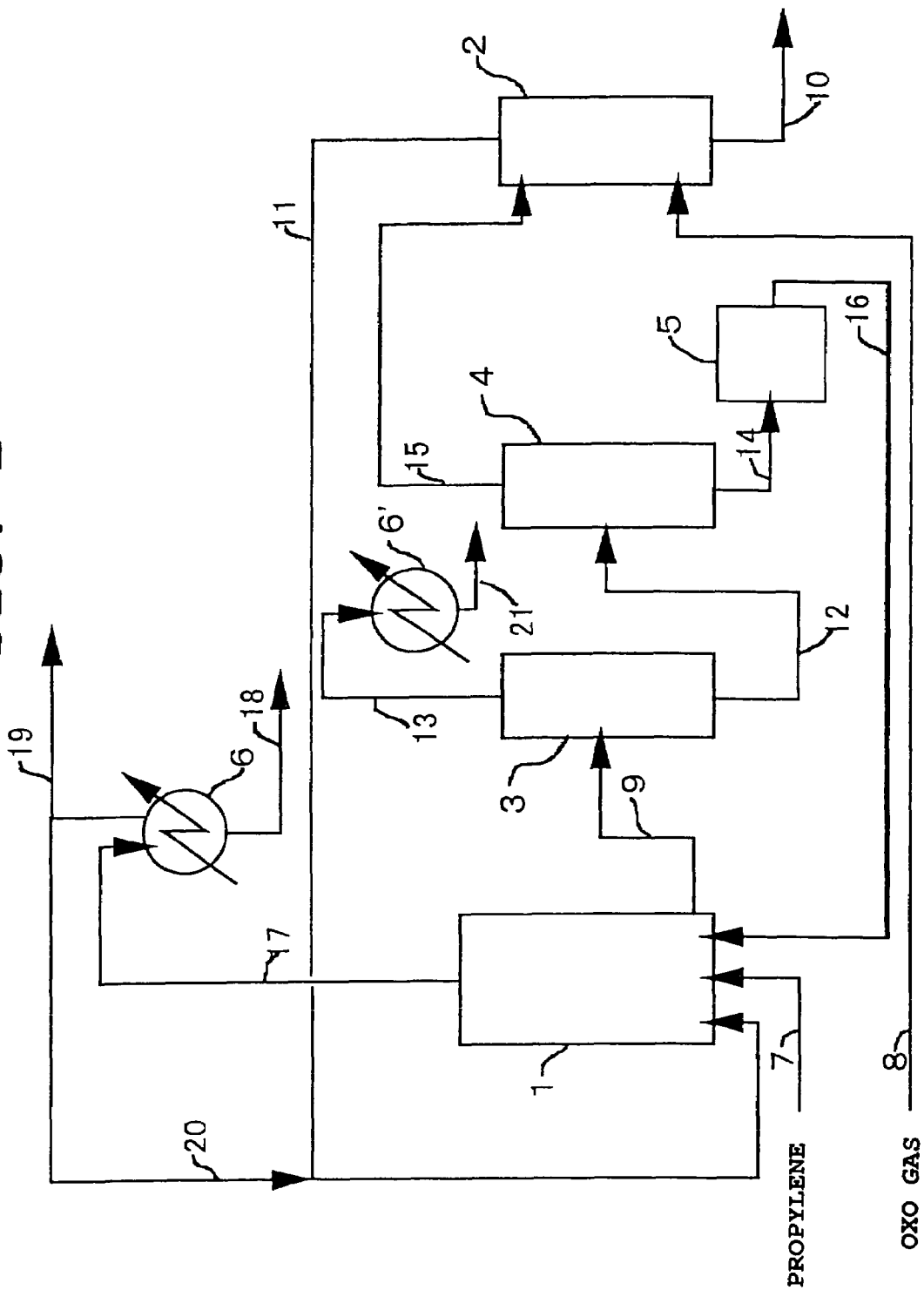
FIG. 2 is a process flow sheet showing another embodiment of a process of the invention.
Figure 3:
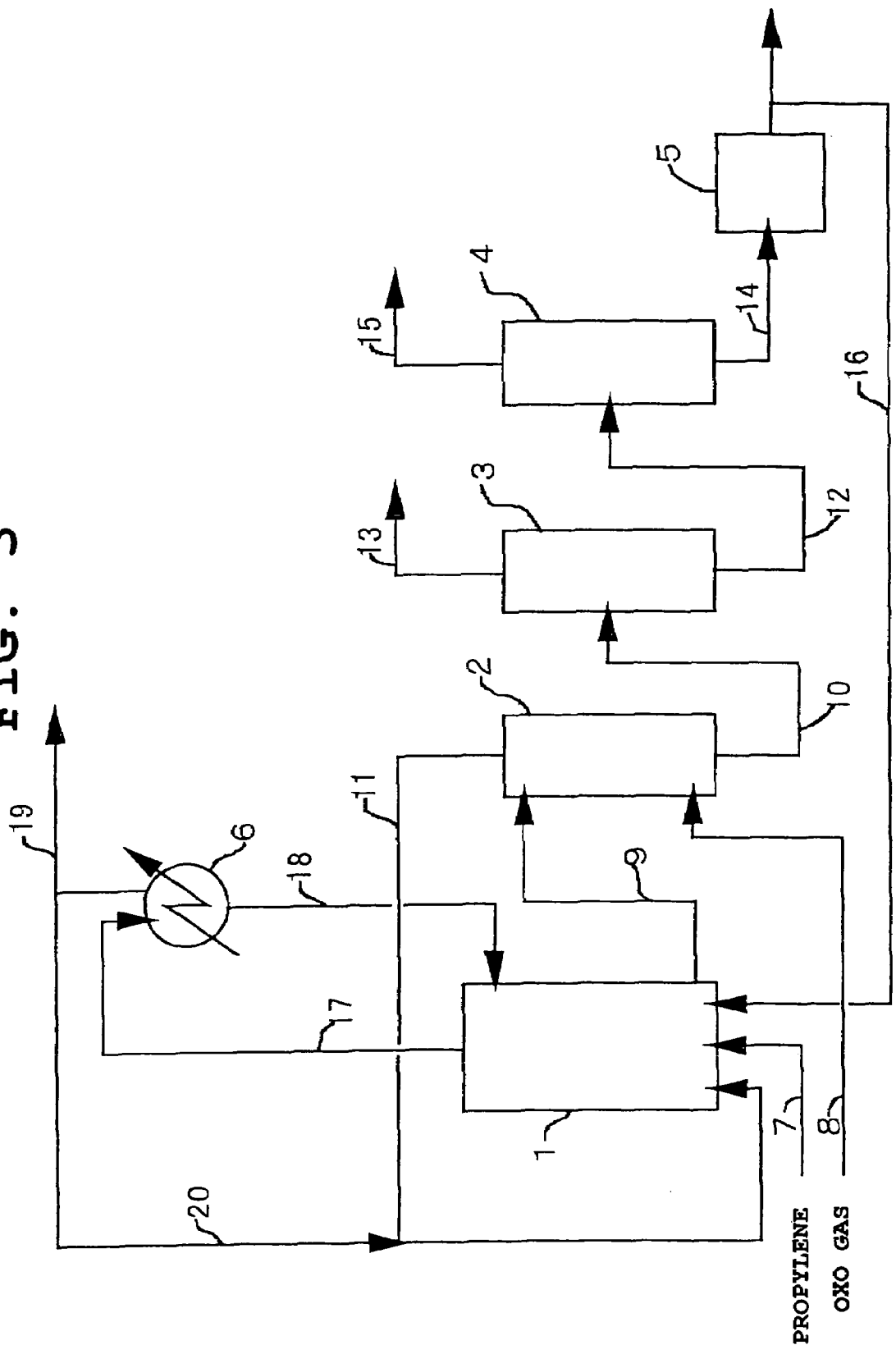
FIG. 3 is process flow sheet of Comparative Example 1.

One and another specific embodiments of the process of the invention will be described below with reference to FIGS. 1 and 2, respectively. In FIGS. 1 and 2, numerals 1, 2, 3, 4 and 5 denote a reactor, a counter-current contact column for recovery of unreacted olefinic unsaturated compound, a gas-liquid separator, a catalyst separation column, and a catalyst recovery step, respectively.

In the embodiment of FIG. 1, an olefinic unsaturated compound is continuously fed into a reactor 1 through a conduit 7, and a catalyst liquid is circulated and fed into the reactor 1 through a conduit 16. Further, an oxo gas is continuously fed into a counter-current contact column 2 though a conduit 8 and after recovering the unreacted olefinic unsaturated compound, is fed into the reactor 1 through a conduit 11, thereby undergoing a hydroformylation reaction. A reaction product liquid containing an aldehyde product, a catalyst, water, a solvent, etc. is introduced into the counter-current contact column 2 through a conduit 9 and then brought into counter-current contact with the oxo gas. A bottom liquid of the counter-current contact column after recovering the unreacted olefinic unsaturated compound is fed into a gas-liquid separator 3 through a conduit 10 and after separating the oxo gas, etc. through a conduit 13, is introduced into a catalyst separation column 4 through a conduit 12; and the aldehyde product, etc. are distilled out and separated through a conduit 15, whereby the aldehyde product is recovered further through a rectification column, etc. On the other hand, the liquid containing the catalyst and solvent is taken out through a conduit 14 and if desired, after passing through a catalyst recovery step 5, is circulated into the reactor 1. The process of the invention is concerned with such a process in which a mixed vapor flow comprising the aldehyde product, water and unreacted olefinic unsaturated compound is taken out from the reactor 1 through a conduit 17 and cooled by a condenser 6, and a part or the whole of the resulting condensate is taken through a conduit 18 outside the catalyst-existent region. Further, the uncondensed gas is circulated into the reactor 1 through a conduit 20, and a part of the gas is purged through a conduit 19.

In the embodiment of FIG. 2, a reaction product liquid taken out from a reactor 1 through a conduit 9 is first introduced into a gas-liquid separator 3; the gas component is separated through a conduit 13; the liquid phase is introduced into a catalyst separation column 4 through a conduit 12; an aldehyde product is distilled out through a conduit 15, introduced into a counter-current contact column 2, and then brought into counter-current contact with an oxo gas introduced through a conduit 8 to separate the unreacted olefinic unsaturated compound; and an aldehyde is recovered through a conduit 10. On the other hand, the unreacted olefinic unsaturated compound is fed into the reactor 1 through a conduit 11. With respect to a liquid containing a catalyst and a solvent obtained from the column bottom of the catalyst separation column 4, the liquid containing the catalyst and the solvent is taken out through a conduit 14 and if desired, after passing through a catalyst recovery step 5, is circulated into the reactor 1 through a conduit 16. The process of the invention is concerned with such a process in which a mixed vapor flow comprising the aldehyde product, water and unreacted olefinic unsaturated compound is taken out from the reactor 1 through a conduit 17 and cooled by a condenser 6, and a part or the whole of the resulting condensate is taken out through a conduit 18 outside the catalyst-existent region. Further, the uncondensed gas is circulated into the reactor 1 through a conduit 20, and a part of the gas is purged through a conduit 19. Moreover, a gas separated from the gas-liquid separator 3 is also cooled by a condenser 6', and a part or the whole of the resulting condensate can be taken out outside the catalyst-existent region through a conduit 21.

EXAMPLES

The invention will be more specifically described below with reference to the Examples. However, it should be construed that the invention is never limited to these Examples unless exceeding the gist of the invention.

Example 1

A hydroformylation reaction of propylene was carried out using an apparatus of FIG. 1. The reaction was carried out in the presence of a rhodium-bisphosphite based complex catalyst (Rh concentration: 500 mg/l, P/Rh (molar ratio)=8). The following compound (1) was used as a bisphosphit ligand.

Compound (1)

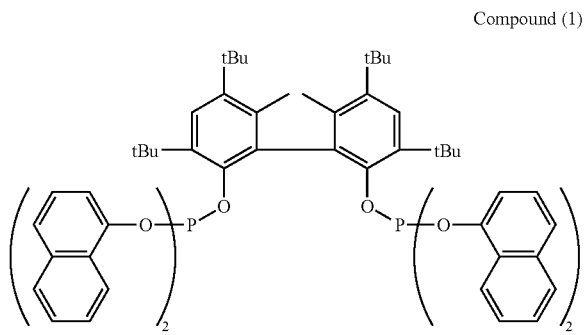

(In the formula, tBu represents a t-butyl group, and -represents a methyl group.)

Propylene was continuously fed into the reactor 1 through the conduit 7, and a catalyst liquid was circulated and fed in an amount of 7,620 kg/hr through the conduit 16. Further, an oxo gas ($H_2/CO=1.0$) containing 0.4% by weight of water was continuously fed into the counter-current contact column 2 through the conduit 8 and after recovering unreacted propylene, was fed into the reactor 1 through the conduit 11. The reactor was kept at 90° C. and at a total pressure of 10 kg/cm$^2$, and the feed amounts of propylene and oxo gas were adjusted such that the pressure of the reactor was kept at 10 kg/cm$^2$. As a result, the feed amount of propylene was 1,200 kg/hr, and the feed amount of oxo gas was 900 kg/hr. The unreacted olefin, unreacted gas, aldehyde product and water were partially taken out as a mixed vapor flow from the reactor vapor phase and cooled to 40° C. by the condenser 6, and the resulting condensate was purged in an amount of 1,730 kg/hr outside the catalyst-existent region through the conduit 18. A part of the vent gas from the condenser vapor phase was purged through the conduit 19, and the residue was recirculated in an amount of 5,000 kg/hr into the reactor 1 through the conduit 20. The reaction product liquid was introduced into the counter-current column 2 through the conduit 9 and brought into intimate contact with the oxo gas to subject unreacted propylene to gas stripping, and then introduced into the gas-liquid separator 3 and reduced in pressure. After gas-liquid separation, the reaction mixture was introduced into the catalyst separation column 4, the aldehyde product was distilled out from the column top, and the catalyst liquid from the column bottom was passed through the catalyst recovery step 5 including a water washing step through the conduit 14 and then recirculated into the reactor 1 through the conduit 16. The water concentration at an outlet of the catalyst recovery step 5 was 1.6% by weight. At this time, the water concentration in the reactor was 1.0% by weight.

Comparative Example 1

A hydroformylation reaction of propylene was carried out using the same apparatus as in Example 1. The same operation conditions and reaction conditions as in Example 1 were employed, except that the condensate of the condenser 6 was returned into the reactor 1 without being purged outside the catalyst-existent region. At this time, the water concentration in the reactor was 1.5% by weight.

While the invention has been described in detail and with reference to specific embodiments thereof, it will be apparent to one skilled in the art that various changes and modifications can be made therein without departing from the spirit and scope thereof.

This application is based on a Japanese patent application filed Mar. 8, 2001 (Japanese Patent Application No. 2001-064880), the contents of which are incorporated herein by reference.

INDUSTRIAL APPLICABILITY

According to the invention, it is possible to provide a process of suppressing decomposition of phosphite ligands within a catalyst-existent region in the continuous hydroformylation process using a general rhodium-phosphite based complex as a catalyst, especially to provide a process of producing aldehydes efficiently and economically by suppressing decomposition of ligands in the hydroformylation reaction using a rhodium-phosphite based complex catalyst, while enabling to reduce the water concentration within a catalyst-existent region that will become a cause of decomposition of phosphite ligands by 30% or more.

The invention claimed is:

1. A process of producing aldehydes in a continuous hydroformylation process of continuously reacting an olefinic unsaturated compound with carbon monoxide and hydrogen in the presence of a rhodium-phosphite based complex catalyst and continuously separating at least one component from a reaction product, the process being characterized in that at least a part of an aldehyde product and water are taken out as a mixed vapor flow from a catalyst-existent region in the process, and at least a part thereof is fed outside the catalyst-existent region as it stands as the vapor or as a condensate after cooling, to reduce the water concentration within the catalyst-existent region.

2. The process of producing aldehydes according to claim 1, wherein the continuous hydroformylation process is a liquid circulation type hydroformylation process in which a reaction product containing at least the rhodium-phosphite based complex catalyst and aldehyde product taken out from a reactor is fed into a catalyst separation step to separate the aldehyde product, followed by circulation into the reactor.

3. A process of producing aldehydes in a liquid circulation type hydroformylation process of taking out a reaction product containing at least a rhodium-phosphite based complex catalyst and an aldehyde product obtained by continuous hydroformylation reaction of an olefinic unsaturated compound with carbon monoxide and hydrogen in the presence of a rhodium-phosphite based complex catalyst from a reactor and feeding it into a counter-current contact column; subjecting it to counter-current contact with a raw material gas to recover the unreacted olefinic unsaturated compound; and after gas-liquid separation, subjecting a liquid phase to separation and recovery of the aldehyde product in a catalyst separation step and then circulating it as a reaction medium into the reactor, the process being characterized in that at least a part of the aldehyde product and water are taken out as a mixed vapor flow from a catalyst-existent region in the process, and at least a part of the mixed vapor flow is taken out as it stands as the vapor or as a condensate after cooling and then fed into a step outside the catalyst-existent region to reduce the water concentration within the catalyst-existing region.

4. A process of producing aldehydes in a liquid circulation type hydroformylation process of taking out a reaction product containing at least a rhodium-phosphite based complex catalyst and an aldehyde product obtained by continuous hydroformylation reaction of an olefinic unsaturated compound with carbon monoxide and hydrogen in the presence of a rhodium-phosphite based complex catalyst from a reactor; after gas-liquid separation, subjecting the resulting liquid phase to separation and recovery of the aldehyde product in a catalyst separation step and then circulating it as a reaction medium into the reactor; and bringing the aldehyde product separated in the catalyst separation step into counter-current contact with a raw material gas in a counter-current contact column to recover the unreacted olefinic unsaturated compound, the process being characterized in that at least a part of the aldehyde product and water are taken out as a mixed vapor flow from a catalyst-existent region, and at least a part thereof is fed as it stands as the vapor or as a condensate after cooling into a step outside the catalyst-existent region to reduce the water concentration within the catalyst-existing region.

5. The process of producing aldehydes according to claim 4, wherein at least a part of the mixed vapor flow containing at least a part of the aldehyde product and water taken out from the catalyst-existent region is taken out as it stands as the vapor or as a condensate after cooling and then fed into the counter-current contact column.

6. The process of producing aldehydes according to claim 1, wherein the continuous hydroformylation process is a fixed catalyst type continuous hydroformylation process in which a reaction product containing the aldehyde product, unreacted olefinic unsaturated compound and by-products taken out from a reactor is fed into a separation step to separate the aldehyde product.

7. The process of producing aldehydes according to claim 6, wherein the amount of the aldehyde contained in the reaction medium and a high-boiling product formed in the reaction process in the reactor is 0.6 or more in terms of a weight ratio of aldehyde/high-boiling product.

8. The process of producing aldehydes according to claim 6, wherein the continuous hydroformylation process includes a catalyst reactivation step.

9. The process of producing aldehydes according to claim 1, wherein the olefinic unsaturated compound is reacted with carbon monoxide and hydrogen at a temperature of from 30° C. to 90° C.

10. The process of producing aldehydes according to claim 1, wherein at least a part of the aldehyde product and water are taken out as a mixed vapor flow from the reactor and a gas-liquid separator equipped in the reactor, and at least a part thereof is fed as it stands as the vapor or as condensate after cooling outside the catalyst-existent region, thereby reducing the water concentration within the catalyst-existent region.

11. The process of producing aldehydes according to claim 1, wherein the amount of water contained in the mixed vapor flow to be taken out from the catalyst-existent region is 30% or more of the amount of water to be fed into the reactor and water to be formed within the reactor, and at least a part of water contained in the mixed vapor flow is fed outside the catalyst-existent region.

12. The process of producing aldehydes according to claim 1, wherein the amount of water contained in the mixed vapor flow to be taken out from the catalyst-existent region is 30% or more of the amount of water to be fed into the reactor and water to be formed within the reactor, and 30% or more of the amount of water contained in the mixed vapor flow is fed outside the catalyst-existent region.

13. The process of producing aldehydes according to claim 1, wherein the amount of water to be fed outside the catalyst-existent region is 30% or more of the amount of water to be fed into the reactor and water to be formed within the reactor.

14. The process of producing aldehydes according to claim 1, wherein the olefinic unsaturated compound is propylene.

* * * * *